US00PP32390P2

(12) United States Plant Patent
Olesen

(10) Patent No.: US PP32,390 P2
(45) Date of Patent: Oct. 27, 2020

(54) COMPACT FLORIBUNDA ROSE PLANT NAMED 'POULCAS059'

(50) Latin Name: ***Rosa* hybrid**
Varietal Denomination: Poulcas059

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/602,261

(22) Filed: Sep. 3, 2019

(51) Int. Cl.
*A01H 5/02* (2018.01)
*A01H 6/74* (2018.01)

(52) U.S. Cl.
USPC ..... Plt./145
CPC ..... *A01H 6/749* (2018.05)

(58) Field of Classification Search
USPC ..... Plt./145
CPC ..... A01H 6/749; A01H 5/02
See application file for complete search history.

*Primary Examiner* — Keith O. Robinson

(57) ABSTRACT

A new garden rose plant of the Compact Floribunda class which has abundant, yellow blend flowers and attractive foliage. This new and distinct variety has shown to be uniform and stable in the resulting generations from asexual propagation.

1 Drawing Sheet

Botanical designation: *Rosa* hybrid.
Variety denomination: 'Poulcas059'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2009 and the resulting seeds were planted in a controlled environment in Fredensborg, Denmark. The new variety, named 'Poulcas059', originated as a single seedling from the stated cross.

The new variety may be distinguished from its male pollen parent and female seed parent primarily by the following characteristics. The male pollen parent plant has an overall growth height of 125 cm while the new variety has an overall growth height of 30 to 40 cm. The female seed parent plant has an overall growth height of 45 cm while the new variety grows to 30 to 40 cm.

The objective of the hybridization of this rose variety was to create a new and distinct variety with unique qualities, such as:

1. Uniform and abundant yellow blend flowers;
2. Vigorous, but compact growth when propagated on its own roots;
3. Exceptional disease resistance.

This combination of qualities is not present in previously available commercial cultivars of this type, known to the inventor, and distinguish 'Poulcas059' from all other varieties of which we are aware.

As part of the rose development program, Mogens N. Olesen germinated the seeds from the aforementioned hybridization during winter of 2009 and conducted evaluations on the resulting seedlings in a controlled environment in Fredensborg, Denmark. 'Poulcas059' was selected in the spring of 2010 by the inventor as a single plant from the progeny of the aforementioned hybridization.

Asexual reproduction of 'Poulcas059' by rooted cuttings was first done by Mogens N. Olesen in the nursery in Fredensborg, Denmark in July, 2010. This initial and other subsequent asexual propagations conducted in controlled environments have demonstrated that the characteristics of 'Poulcas059' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcas059'. Specifically illustrated in the drawing is an open flower viewed from above and the side. Also illustrated are flower buds, sepals detached, mature and juvenile leaves, and a bare stem. Plants shown are 2 years of age.

DETAILED DESCRIPTION OF THE VARIETY

The following is a description of 'Poulcas059',as observed in its growth in a field nursery in Linn County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpar090', U.S. Plant Pat. No. 28,044 are compared to 'Poulcas059' in Chart 1.

CHART 1

| | 'Poulcas059' | 'Poulpar090' |
|---|---|---|
| Petal Count | 40 petals | 80 petals |
| Flower Diameter | 45 mm | 70 mm |

CHART 1-continued

| | 'Poulcas059' | 'Poulpar090' |
|---|---|---|
| General Tonality of Flower Color | Open flowers are Yellow-Orange Group 15A and Orange Group 24A | Yellow-Orange Group 20D |

FLOWER AND FLOWER BUD

Blooming habit: Continuous.

Flower bud:

*Size.*—Upon opening, 23 mm in length from base of receptacle to end of bud. Bud diameter is 12 mm.

*Bud form.*—Ovoid.

*Bud color.*—As sepals divide petals are Yellow-Orange Group 16B, with intonations of Orange-Red Group 32A.

*Sepal inner surface.*—Color: Yellow-Green Group 146D with anthocyanic intonations of Greyed-Red Group 180B. Surface: Lightly pubescent.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have moderate foliaceous appendages on three of the five sepals.

*Sepal size.*—24 mm long, 6 mm wide.

*Receptacle.*—Texture: Smooth. Size: 5 mm in height, 5 mm wide. Color: Yellow-Green Group 144A. Shape: Funnel.

*Pedicel.*—Surface: Smooth. Length: 33 mm. Diameter: 2 mm on average. Color: Yellow-Green Group 144A. Strength: Strong.

Flower bud development: Flower buds are borne in clusters of about 5 flower buds per stem.

Flower bloom:

*Fragrance.*—Moderate.

*Duration.*—The blooms have a duration on the plant of approximately 10 days. Petals fall cleanly away from plant after flowers have fully matured.

*Size.*—Flower diameter is 45 mm when open. Flower depth is 23 mm.

*Flower shape.*—High centered, double, with a high pointed center which is tightly closed.

*Shape of flower, side view.*—The upper portion is a flattened convex. The lower portion is flat.

Petalage: Under normal conditions, flowers have about 40 petals.

General tonality of flower: Open flowers are Yellow-Orange Group 15A and Orange Group 24A.

Petal color:

*Upon opening, and after opening, outer petals.*—Upper surface: At the basal zone, Yellow Group 12A. Intonations of Orange Group 28C at middle and marginal zone. Lower surface: Yellow Group 10A, with some intonations of Orange Group 29A.

*Upon opening, and after opening, inner petals.*—Upper surface: At the basal zone, Yellow Group 12A. Intonations of Orange Group 28C at middle and marginal zone. Lower surface: Yellow Group 10A, with some intonations of Orange Group 29A.

Petals:

*Petal reflex.*—Lightly reflexed.

*Margin.*—Entire and uniform.

*Shape.*—Broad and elliptic. Apex shape: Rounded. Base shape: Rounded.

*Size.*—25 mm (l)×25 mm (w).

*Texture.*—Smooth.

*Thickness.*—Average.

Petaloids:

*Size.*—20 mm (l) by 14 mm (w).

*Quantity.*—About 5.

*Shape.*—Rounded, with an acute base and rounded apices.

*Color.*—Undersurface is Yellow Group 11A shaded with Orange Group 24C. The upper surface is Yellow-Orange Group 14A shaded with Orange Group 28B.

Reproductive flower parts:

*Pollen.*—None observed.

*Anthers.*—Size: 2 mm in length. Color: Yellow-Orange Group 17B. Quantity: 34 on average.

*Filaments.*—Color: Yellow Group 13A. Length: 4 mm.

*Pistils.*—Length: 5 mm. Quantity: 21 on average.

*Stigmas.*—Color: Greyed-Yellow Group 160A.

*Styles.*—Color: Greyed-Red Group 179B.

*Location of stigmas.*—Inferior in location relative to the length of the filaments and the height of the anthers.

*Hips.*—None Observed.

PLANT

Plant growth: Upright and bushy. Plants are 30 to 40 cm in height, and 27 cm wide.

Stems:

*Color of juvenile growth.*—Yellow-Green Group 144B.

*Color of mature growth.*—Yellow-Green Group 144A.

*Length.*—Canes are about 15 cm from the base of the plant to the flowering portion.

*Diameter.*—About 4 mm.

*Internodes.*—On mature canes about 23 mm between nodes.

*Surface texture.*—Young wood: Smooth. Older wood: Smooth.

Long prickles:

*Incidence.*—3 prickles per 10 cm of stem.

*Size.*—Average length of prickles on mature stems is 4 mm.

*Shape.*—Upper portion is linear. Lower portion is concave.

*Color.*—Juvenile prickles: Greyed-Red Group 179C. Mature prickles: Greyed-Red Group 179C.

Plant foliage:

*Compound leaf.*—105 mm (l)×80 (w).

*Quantity.*—3 or 4 leaves per 10 cm of stem on average.

*Leaf bearing angle to the stem:* 45 degrees.

*Color of juvenile foliage.*—Upper side: Yellow-Green Group 144A shaded with Greyed-Red Group 178A. Lower side: Yellow-Green Group 144B shaded with Greyed-Red Group 178A.

*Color of mature foliage.*—Upper side: Yellow-Green Group 147A. Lower side: Yellow-Green Group 147C.

Plant leaves and leaflets:

*Stipules.*—Size: 20 mm long, 4 mm wide. Quantity: 2 per compound leaf. Shape: Linear, slightly broad based with outward extending apices. Margins: Finely serrated. Color: Yellow-Green Group 144A.

*Petiole*.—Length: 25 mm. Diameter: 2 mm. Upper surface color: Yellow-Green Group 144A. Lower surface color: Yellow-Green Group 144A.

*Rachis*.—Length: 31 mm. Upper surface color: Yellow-Green Group 144A with intonations of Greyed-Red Group 178A. Lower surface color: Yellow-Green Group 144A.

*Leaflet*.—Quantity: Normally 5, occasionally 7 leaflets. Margins: Serrated. Size: Terminal leaflets are about 41 mm long, 34 mm wide. Shape: Generally elliptical. Base: Rounded. Apex: Mucronate. Texture: Smooth. Thickness: Average. Arrangement: Odd pinnate. Venation: Reticulate. Glossiness: Glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Compact Floribunda rose class named 'Poulcas059', substantially as illustrated and described herein, due to its abundant yellow blend flowers, disease resistance, and extended period of bloom.

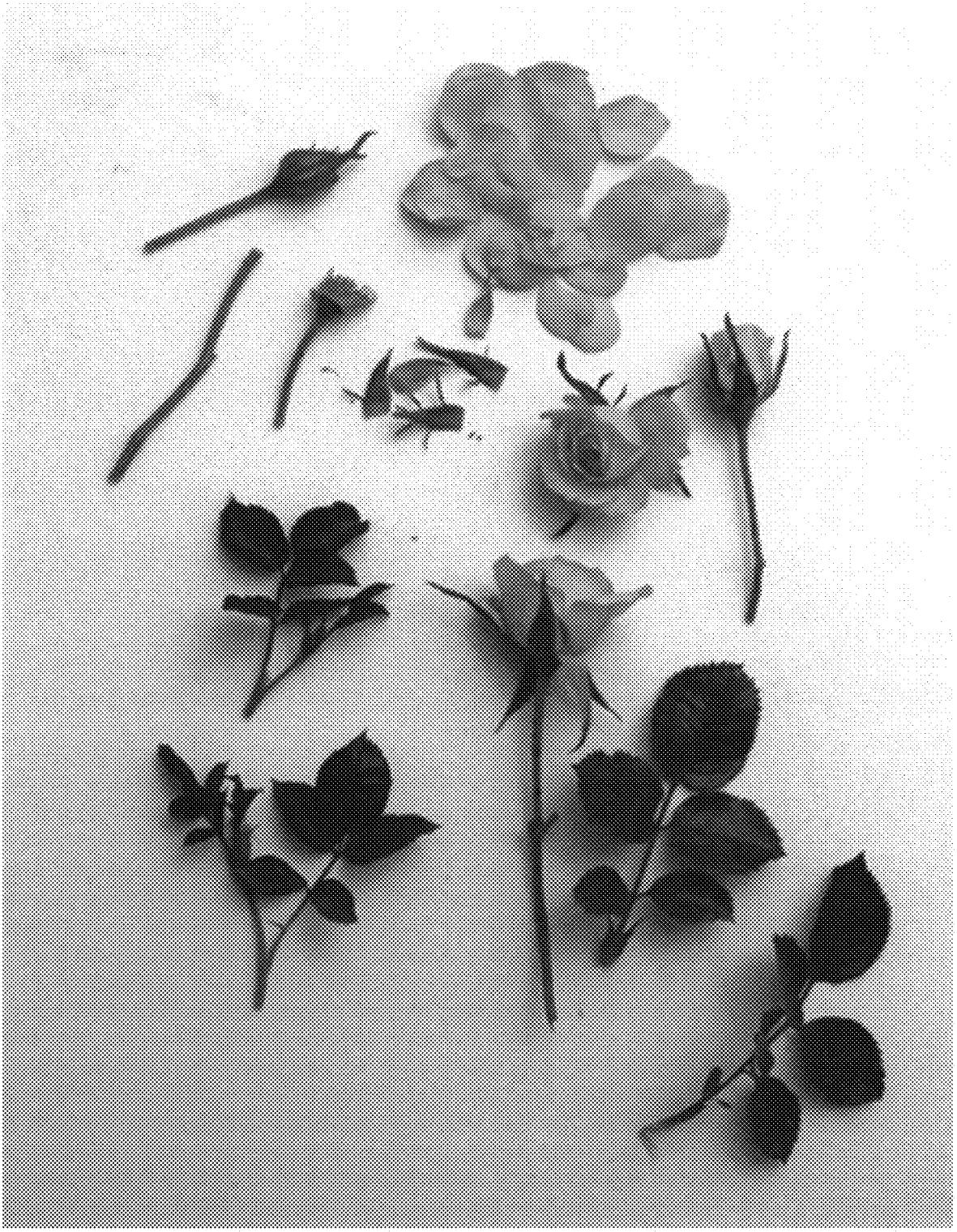

* * * * *